United States Patent [19]

Adams et al.

[11] 4,416,998

[45] Nov. 22, 1983

[54] SILVER STAIN PROCEDURE AND KIT FOR SAME

[75] Inventors: Lonnie D. Adams, Gobles; David W. Sammons, Kalamazoo, both of Mich.

[73] Assignee: The Upjohn Company, Kalamazoo, Mich.

[21] Appl. No.: 359,339

[22] Filed: Mar. 17, 1982

Related U.S. Application Data

[63] Continuation-in-part of Ser. No. 250,512, Apr. 2, 1981, abandoned.

[51] Int. Cl.$^3$ ............................................. G01N 33/68
[52] U.S. Cl. ...................................... 436/86; 422/61; 436/63; 436/174
[58] Field of Search ........................... 436/63, 86, 174; 422/61

[56] References Cited

U.S. PATENT DOCUMENTS 4,239,495  12/1980  Gindler ................................. 424/3

OTHER PUBLICATIONS

C. R. Merril et al., Anal. Biochem., 110(1), 201-207 (1981).
D. Goldman et al., Clin. Chem., 26(9), 1317-1322 (1980).

*Primary Examiner*—Sidney Marantz
*Attorney, Agent, or Firm*—L. Ruth Hattan

[57] ABSTRACT

A silver stain procedure wherein a substance capable of binding silver is treated with a glutaraldehyde solution, an aqueous silver salt solution, a reducing solution and an aqueous carbonate or sulfate solution and kit useful in practicing same.

13 Claims, No Drawings

SILVER STAIN PROCEDURE AND KIT FOR SAME

CROSS REFERENCE TO RELATED APPLICATION

This application is a continuation-in-part of copending application Ser. No. 250,512, filed Apr. 2, 1981 now abandoned.

FIELD OF INVENTION

The pesent invention involves a novel silver staining method and a kit useful in practicing said method.

BACKGROUND OF INVENTION

There are a number of known methods useful in staining proteins which utilize silver. For example, L. Kerenyi, et al., Clin. Chim. Acta 38, 465–467 (1972) describes a method for demonstrating proteins in electrophoretic, immunoelectrophoretic and immunodiffusion preparations whereby the preparations are treated with potassium ferrocyanide which is transformed during development into silver ferrocyanide then into colloidal silver grains. The physical developer contains anhydrous sodium carbonate, ammonium nitrate, silver nitrate, tungstosilicic acid and formalin, and the protein in the preparations stain dark brown with a pale gray background.

R. C. Switzer, et al., Anal. Biochem. 98, 231–237 (1979) and C. R. Merril, et al., Proc. Nat'l. Acad. Sci. U.S.A., 76, No. 9, 4335–4339 (1979) describe a silver stain technique for detecting proteins and peptides in polyacrylamide gel which is a modification of de Olmos' neural, cupric-silver stain. The procedure consists of ten steps and utilizes an aqueous solution of silver nitrate and cupric nitrate and involves treatment with a diammine solution which is known to sometimes form an explosive silver amide complex. The proteins stain as dark spots on a darkened background.

B. A. Oakley, et al., Anal. Biochem. 105, 361–363 (1980) simplified the above procedure of Switzer, et al., by reducing the number of steps involved to six and also reducing the amount of silver required without diminishing the sensitivity of the technique. However, the manner in which the proteins stain was not changed, i.e., dark stain on a darkened background.

A further modification of the Switzer, et al., procedure was made by R. C. Allen, Electrophoresis I, 32–37 (1980) who increased the sodium to ammonium ion ratio which resulted in increased silver deposition.

C. R. Merrill, et al., Anal. Biochem. 110, 201–207 (1981) modified and simplified the above procedure of Kerenyi, et al., adapting it to acrylamide gels.

D. Goldman, et al., Clin. Chem. 26, No. 9, 1317–1322 (1980) report that when using a procedure essentially the same as that of Merrill, et al., (PNAS, 1976) and Switzer, et al., (Anal. Biochem., 1979) proteins from samples of cerebral spinal fluid stained in shades of yellow, red and blue.

C. R. Merrill, et al., Science 211, 1437–1438 (1981) describe a silver stain procedure for proteins separated by two dimensional gel electrophoresis which requires treatment with potassium dichromate and nitric acid prior to staining with silver nitrate followed by washing then immersion in an image developer containing formalin and sodium carbonate. There is no indication of color development with this stain procedure.

Poehling and Neuhoff, Electrophoresis 1981, 2, 141–147, describe a silver stain suitable for acrylamide gels of 0.5 to 1 mm thickness which requires a pretreatment with glutardialdehyde under controlled temperatures prior to staining with a diamine solution.

Marshall and Latner, Electrophoresis 1981, 2, 228–235, describe a silver stain method which requires a treatment with paraformaldehyde and sodium cacodylate prior to staining with a modified diamine solution wherein methylamine is substituted for ammonium hydroxide. Ochs, et al., Electrophoresis 1981, 2, 304–307, and Sammons and Adams, Electrophoresis 1981, 2, 135–145, describe a silver stain procedure of which the present invention is a modification.

With the exception of the 1980 Goldman, et al., procedure and the method of Sammons and Adams all of the silver stain techniques known heretofore only stain proteins in varying shades of brown or black.

The present invention provides a unique stain procedure which not only is highly sensitive, but also, enables one to stain a variety of substances including proteins in varying shades of color.

SUMMARY OF INVENTION

The present invention is a method for staining various types or classes of compounds which is highly sensitive enabling one to detect picogram quantities of compounds or substances, and also is unique in that the method imparts color to the various substances staining them in varying shades of blue, green, red, and yellow. The present method will stain any substance that is capable of binding silver.

The present invention provides a novel method for staining substances capable of binding silver and which are supported in or on a matrix which comprises the steps of oxidizing said substance with a glutaraldehyde solution, washing with water, equilibrating said substance in a suitable silver salt solution, then subjecting said substance to a reducing solution, and immersing said substance in a first, then a second and third sulfate or carbonate salt solution.

The present method is particularly suited for staining proteins. The present method is particularly useful in enhacing stain sensitivity in ultrathin gel preparation. The color can be achieved by prolonging the reduction step and adds a new dimension to the separation and identification of proteins, as well as other substances, by electrophoresis by aiding for example in the resolution of overlapping proteins and identifying members of a family of proteins by their characteristic color. Thus the method of the present invention which is both sensitive and reproducible will facilitate the identification of substances or compounds that are diagnostic markers and/or primary lesions of most genetic diseases including the major diseases such as diabetes, atherosclerosis and cancer. In addition, pathological changes in tissues can be correlated with changes in certain substances, particularly proteins. The present invention provides a means to enhance ones understanding of normal and disease conditions. Also, the present method is particularly useful in detecting minute amounts of proteins separated from samples required by forensic medicine.

Another aspect of the present invention is a kit wherein the component parts are assembled in a manner to facilitate the practice of the silver staining method of the present invention, said kit comprising multiple containers having therein appropriate amounts of reagents necessary to practice said method as follows:

(a) a container having therein a solution of 2.5–25% glutaraldehyde;
(b) a container having therein a suitable silver salt;
(c) a container having therein an appropriate base solution;
(d) a container having therein an aldehyde solution; and
(e) a container having therein an appropriate amount of a carbonate or sulfate salt.

Generally the quantity of oxidizing reagent contained in the kit for 10 gels (8 cm×7 cm×0.1 mm) will be: 60 ml of a solution of 25% glutaraldehyde; the quantity of silver salt contained in the kit will be up to 0.6 grams and preferably will be 0.4 to 1.0 grams; the quantity of base will vary from 100 to 150 ml; the quantity of aldehyde will vary from about 0.50 to 2.0 ml; and the amount of carbonate or sulfate salt will vary from about 0.5 to 2.0 grams. The glutaraldehyde solution is buffered with 1 to 2% of sodium cacodylate, pH 7.3.

DETAILED DESCRIPTION OF INVENTION

The method of the present invention is useful to stain any substance or compound which is capable of binding silver. Such substances include proteins, polypeptides, amino acids, nucleic acids and polymers thereof, lipids, carbohydrates including starches and sugars of various classes, e.g., oligosaccharides, or polysaccharides, such as mucoitin sulfate, lipoproteins, glucoproteins, nucleoproteins, including ribonucleic- and deoxyribonucleic-protein complexes, mucopolysaccharides, e.g., chondroitin, proteoglycans, mucolipids, such as ganglioside, mucoproteins, and glycolipids. We have found that the present method is particularly useful in identifying families of proteins, i.e., proteins comprised of the same protein subunits but which may be conjugated to other chemical entities, such as, a saccharide thereby altering the overall net charge or character of the protein.

It is important when staining the sample of substance supported in a matrix, such substance so supported being referred to hereinafter as "matrix preparation," by the method of the present invention that said matrix preparation be washed thoroughly to remove any components which may interfere with the uptake of silver by the substance to be stained. The matrix preparation should be washed repeatedly, for example, in a lower alkanol, such as methanol or ethanol containing a mild acid, such as, trichloroacetic acid or acetic acid. Generally, for a 0.1 mm thick gel, washing for 1 to 3 hours is adequate with several changes of solution using for each milliliter (ml) of matrix 15 ml of solution per change. Of course, less time is required for thinner gels. This washing procedure is commonly referred to as fixation/washing.

The present novel staining method can be used to stain virtually any substance which is capable of binding silver and typically is useful in staining such substances which have been separated using one or two dimensional electrophoresis techniques. The matrix in which the substance to be stained is supported can be comprised of any materials which are commonly used in electrophoretic procedures. For example, the matrix may consist of derivatized paper that is useful for electrophoretic protein transfer, cellulose acetate, starch gel, agarose, Sephadex beads, or polyacrylamide, and may vary in thickness from an ultrathin matrix of about 0.05 mm to 0.5 mm. It may be desirable to attach the matrix on a nylon mesh, a glass plate, or a plastic sheet for additional support. As is known from standard electrophoretic techniques, the density and pore size of the matrix may also vary. A preferred matrix composition is polyacrylamide, varying from 0.05 mm to 0.5 mm in thickness with 80–100$\mu$ being the most preferred thickness.

We have found that the present method is especially useful for staining substances, and, in particular, proteins that have been separated by two dimensional electrophoresis on polyacrylamide gels. The method of the present invention is particularly useful for staining substances separated on ultrathin gels prepared by the method of Gorg, et al., Anal. Biochem, 1979, 89, 60–70, and Radola, Electrophoresis, 1980, 1, 43–56.

With the method of the present invention we have been able to detect picogram quantities of substances and obtain matrix preparations which stain in varying shades of blue, green, yellow and red. The background of the matrix preparation stains in light shades of yellow to orange upon which the brightly colored substances are detected easily. The intensity of the color will vary somewhat with the thickness of the matrix as well as with the concentration of the substance to be stained. For best results a matrix of 0.5 mm thickness of 10% to 20% polyacrylamide gel is used.

The novel silver stain procedure described and claimed herein is highly sensitive, gives high resolution of substances, is reproducible, is easy to use, and is efficient in that matrix preparations can be stained batch-wise. Additionally the entire procedure is carried out at room temperature, i.e., about 18° to 27° C. with standard room lighting, there being no requirement of elevated temperatures or special light control.

The oxidizing solution consists of having a concentration of from 2.5 to 20% glutaraldehyde. Generally 3 to 15 ml per gel is used and 1 to 2% (w/v) sodium cacodylate, pH 7.3. Following treatment with glutaraldehyde it is important that the matrix preparation be thoroughly washed with distilled water. Washing for one to 6 hours with changes every 15 to 20 minutes is suitable.

Suitable silver salts which may be used in the present invention are those which will dissociate in water to give free silver ion and which will not complex with the reducing agents employed in the method. Aqueous solutions of silver nitrate or silver acetate are particularly suitable for use in the present invention. The silver salt is dissolved in water, generally distilled water, at a concentration of from about 1 to 6 grams of silver salt per liter of water. The lower concentration of silver salt, i.e., 1 gram/liter results in reduced sensitivity and intensity and the background of the matrix strains lighter than at the higher concentrations of silver salt. Concentrations of silver salt varying from about 3 to 6 grams of salt per liter of water are preferred. The matrix preparation is equilibrated in the silver salt solution for a minimum of about 10 minutes using for each 1 ml of matrix about 15 ml of solution. Of course the thicker matrix preparations require more time to equilibrate than do the thinner matrix preparations.

Following equilibration in the silver salt solution the matrix preparation is subjected to a reducing solution. The reducing solution may be sprayed onto the matrix preparation or the matrix preparation may be immersed in the reducing solution. The reducing solution consists of a base such as aqueous potassium hydroxide or sodium hydroxide and an aldehyde, such as, formaldehyde, acetaldehyde, n-butyraldehyde, or glutaraldehyde. The concentration of base may vary from about 0.5 to 1.0 N with 0.7 N base, preferably sodium hydroxide, being the most suitable. The preferred reducing agent is formaldehyde and generally a 37% solution is employed. Generally the reducing solution will comprise about 0.75 to 1.5 ml of 37% formalin per about each 150 ml of aqueous base. A preferred reducing solution consists of per each 150 ml of 0.75 N NaOH, 1.1 ml of 37% formalin. For each ml of matrix preparation one should use about 15 ml of reducing solution.

It is recommended that in preparing the reducing solution as well as other aqueous solutions described herein one use distilled deionized and degassed water. The reduction generally requires about 30 seconds to 5 minutes, and when the matrix preparation is submersed in the reducing solution agitation at about 40 cycles per minute is recommended. The time required for reduction varies with the thickness of the gels with time required increasing as the matrix thickness increases. The reaction time could be shortened if the temperature is raised. Generally the components of the reducing solution are mixed together and the matrix preparation previously equilibrated in the silver salt solution is brought into contact with the resultant solution.

Following reduction the matrix preparation is immersed for about one to 5 minutes, preferably one minute, in three sequential solutions of 0.075 to 1.5%, preferably 0.75%, anhydrous sodium or potassium carbonate or sodium or potassium sulfate having a pH of 11 or greater. The matrix preparation should then be rinsed with water and air dried. Sodium carbonate is preferred for this step. The stained preparation may be photographed by standard well known techniques.

As indicated hereinabove standard electrophoretic procedures may be used to separate the substances to be stained in either one dimension or two dimensions. When such substances have been separated using standard two dimensional electrophoresis on polyacrylamide gel, it is very important to remove the SDS and electrophoretic buffer salts during the fixation/washing step. Also it is recommended that reagents and water be of highest quality.

When preparing the sample of substance to be stained the concentration for each sample will have to be adjusted individually. Generally, we find that samples should be diluted 10 to 50 times of those used for staining by conventional Coomassie Blue procedures.

A preferred general procedure is the following.

GENERAL PROCEDURE

Tissue samples or samples of substances to be stained are prepared and run on first dimension gels according to the procedures of Gorg, et al., ibid., and Radola, ibid., and second dimension gels according to the procedure described by Anderson and Anderson Anal. Biochem. 85, 331-354 (1978). Second dimension gels are fixed in 50% ethanol/10% acetic acid for two or more hours with one change of fixative. The gels are then washed two times in 25% ethanol/10% acetic acid and 6 times in water with changes every 30 minutes to remove any interfering substances. The gels are then subjected to an oxidizing solution of 5-10% glutaraldehyde for up to 12 hours then washed thoroughly for one to 6 hours with changes every 15 to 20 minutes with distilled water. Next the gels are soaked for about 10 minutes to one hour in 4 g/l $AgNO_3$ in water. Gels are removed from the silver solution and processed singly or in groups of up to 10 or more. Single gels are then placed in a rectangular glass dish $10 \times 10 \times 1$ cm. To this dish is added reducing solution which consists of 15 ml 0.75 N NaOH and 0.1 ml of 37% formaldehyde. The dish is placed on a shaker for 30 seconds, then the reducing solution is poured off and replaced with an equal volume of 0.75% $Na_2CO_3$. The sodium carbonate solution is changed 3 times at one minute intervals. For larger gels, proportionately larger volumes of reducing solution and $Na_2CO_3$ solution and longer treatment times are used.

EXAMPLE 1

Human granulocytes ($10^7$) were solubilized in one ml of 1% Triton X-100. A lysate was prepared by centrifugation $100,000 \times g$ for one hour. A one $mm^2$ square piece of Whatman No. 2 filter paper was saturated with the above protein extract. The filter paper was then placed on an ultrathin gel, $7 \times 8$ cm $\times 100\mu$ thickness and subjected to isoelectric focusing according to the procedure of Allen, Electrophoresis, 1980, Vol. 1, p. 32. The gel was fixed in 12.5% trichloroacetic acid and dried at 60° C. Prior to staining the gel was soaked in distilled water for one hour then placed in 25 ml of 3% glutaraldehyde overnight. The gel was then washed with five changes of distilled water (100 ml per change) for a 6 hour period. The gel was equilibrated in 15 ml of silver nitrate (4 g/l) for 20 minutes. The gel was then placed in a reducing solution comprising 15 ml of 0.75 N sodium hydroxide and 0.1 ml of 37% formaldehyde for 30 seconds with gentle agitation. The reducing solution was then poured off and replaced with 15 ml of 0.75% sodium carbonate for one minute followed by two equal volume changes of 0.75% sodium carbonate solution at one minute intervals. The gel was then removed, rinsed with distilled water and air dried. The separated proteins appeared as brown to black bands on a light amber stained background.

When in the above procedure the gel is left in the reducing solution for 5 minutes the protein bands stain shades of color varying from red, yellow and blue, however it appeared that the sensitivity was decreased.

EXAMPLE 2

The significant reagents for the performance of the staining procedure are assembled into a mercantile kit, specifically, a kit for marketing to qualified individuals to perform the staining procedure. The kit comprises as basic components at least four containers, one of each having therein appropriate amounts of a glutaraldehyde solution; a suitable silver salt; a suitable base; a suitable aldehyde reducing agent; or an appropriate amount of sodium carbonate.

A preferred kit composition is one designed to stain 10 gels which are $7 \times 8$ cm and 0.1 mm thick wherein one container has therein 60 ml of 25% glutaraldehyde; one container has therein 0.6 grams of silver nitrate; another container has therein 9 ml of 50% sodium hydroxide; another container has therein 1.2 ml of 37% formalin; and one additional container has therein 3.4 grams of sodium carbonate.

We claim:

1. A method for staining a substance which is capable of binding silver which is supported in a matrix which comprises the steps of treating said substance with a 2.5-25% glutaraldehyde solution, washing said substance with water, equilibrating said substance in an aqueous silver salt solution, subjecting said substance to a reducing solution, and immersing said substance in multiple and sequential aqueous carbonate or sulfate salt solutions.

2. The method of claim 1 wherein said substance is protein, a polypeptide or a protein containing substance.

3. The method of claims 1 or 2 wherein said substance is subjected to fixation and washing prior to treatment with the glutaraldehyde solution.

4. The method of claim 3 wherein the fixation and washing solution comprises a 12.5% solution of trichloroacetic acid.

5. The method of claims 1 or 2 wherein the matrix is polyacrylamide gel.

6. The method of claim 1 or 2 wherein the silver salt is silver nitrate.

7. The method of claim 1 or 2 wherein the reducing solution comprises a base of either aqueous potassium or sodium hydroxide and formaldehyde.

8. The method of claim 7 wherein a 5% glutaraldehyde solution is employed.

9. The method of claim 1 or 2 wherein said substance is treated with a 2.5 to 25% glutaraldehyde solution for up to 12 hours, then is washed for one to 6 hours in distilled water, is equilibrated in an aqueous silver salt solution for 10 to 120 minutes, after which said substance is subjected to a reducing solution for about 30 seconds to 5 minutes, then is immersed in a first aqueous carbonate or sulfate salt solution for about one to 15 minutes, then a second and third aqueous carbonate or sulfate salt solution for about one to 15 minutes each.

10. The method of claim 9 wherein the carbonate salt is sodium carbonate.

11. A method for staining a protein, polypeptide or protein containing substance which is supported in a matrix which comprises the steps of treating said substance with a 2.5–25% glutaraldehyde solution for one to 6 hours, washing said substance one to 6 hours with distilled water, equilibrating said substance for about two hours in an aqueous silver nitrate solution containing from about 0.5 to 6 grams of silver salts per liter of water, then subjecting said substance for about 30 seconds to 5 minutes to a reducing solution comprising about 0.5 to 2 ml of 37% formalin per about 150 ml of 0.5 to 1.0 N aqueous sodium hydroxide followed by immersing said substance in 3 sequential solutions of 0.075 to 1.5% aqueous sodium carbonate for about one to 5 minutes each.

12. A mercantile kit comprising multiple containers separately holding a concentrated solution of glutaraldehyde, a silver salt, a base solution, an aldehyde solution and a carbonate or sulfate salt.

13. The kit of claim 12 wherein one container has therein a 60 ml 25% glutaraldehyde; one container has therein 0.4 to 1.0 grams of silver nitrate; another container has therein 9 ml of 50% sodium hydroxide; another container has therein 1.2 ml of 37% formalin; and one additional container has therein 3.4 grams of sodium carbonate.

* * * * *